(12) United States Patent  
Goble

(10) Patent No.: US 6,228,081 B1
(45) Date of Patent: May 8, 2001

(54) ELECTROSURGERY SYSTEM AND METHOD

(75) Inventor: Colin C. O. Goble, Penarth (GB)

(73) Assignee: Gyrus Medical Limited, Olt (GB)

( * ) Notice: Subject to any disclaimer, the term of this patent is extended or adjusted under 35 U.S.C. 154(b) by 0 days.

(21) Appl. No.: 09/343,542

(22) Filed: Jun. 30, 1999

(30) Foreign Application Priority Data

May 21, 1999 (GB) .................................................. 9911956

(51) Int. Cl.$^7$ .................................................. A61B 18/04
(52) U.S. Cl. .................................. 606/34; 606/37; 606/41
(58) Field of Search ............................ 606/32–35, 37–42

(56) References Cited

U.S. PATENT DOCUMENTS

| | | |
|---|---|---|
| 4,038,984 | 8/1977 | Sittner . |
| 4,318,409 | * 3/1982 | Oosten . |
| 4,498,475 | * 2/1985 | Schneiderman . |
| 4,727,874 | * 3/1988 | Bowers et al. . |
| 4,996,495 | * 2/1991 | Birx .................................................. 328/65 |
| 5,395,363 | 3/1995 | Billings et al. . |
| 3,885,569 | 5/1997 | Judson . |
| 5,836,943 | * 11/1998 | Miller, III .................................................. 606/34 |
| 6,004,319 | 12/1999 | Goble et al. . |

FOREIGN PATENT DOCUMENTS

| | | |
|---|---|---|
| 1-195 42 418 | 5/1997 | (DE) . |
| 754 427 A2 | 1/1997 | (EP) . |
| 1 321 364 | 6/1973 | (GB) . |
| 1 557 083 | 12/1979 | (GB) . |
| 2 132 893 | 7/1984 | (GB) . |
| 95/18576 AE | 7/1995 | (WO) . |

* cited by examiner

Primary Examiner—Linda C. M. Dvorak
Assistant Examiner—Roy Gibson
(74) Attorney, Agent, or Firm—Oliff & Berridge, PLC

(57) ABSTRACT

An electrosurgical generator has output terminals for connection to active and return electrodes respectively of an electrosurgical instrument and, connected to the output terminals via at least one isolation capacitor, a radio frequency (r.f.) source which may be pulsed by a pulsing circuit. To permit tissue removal at a high rate, the source and the pulsing circuit are arranged so as to generate a pulsed r.f. output signal having a peak-to-peak voltage of at least 1250V, a mark-to-space ratio not more than 1:1, and a pulse length not more than 100 μs.

30 Claims, 5 Drawing Sheets

ELECTROSURGERY SYSTEM AND METHOD

FIELD OF THE INVENTION

This invention relates to an electrosurgery system, an electrosurgical generator, and methods of operating the system and performing electrosurgery.

BACKGROUND OF THE INVENTION

The cutting or removal of tissue electrosurgically using an instrument having a tip with one or more active electrodes supplied with a radio frequency (r.f.) voltage usually involves cell rupture as a result of arcs between the active electrode and the tissue being treated or, in the case of underwater electrosurgery, between the active electrode or electrodes and a conductive liquid such as saline overlying the tissue to be treated. As described in EP-A-0754437, electrode destruction can occur if sufficient radio frequency power is supplied to an electrode to cause burning or melting of the electrode material, and this can be avoided by sensing peak electrode voltage and applying feedback to reduce the applied power so as to set a maximum peak voltage. It will be understood that for a given power setting, the temperature of the electrode depends on the rate at which heat can be dissipated which, in turn, depends on such variables as the degree of tissue engagement, electrode structure, and fluid flow around the electrode. Consequently, to avoid electrode destruction the peak voltage limit must be set at a sufficiently low level to prevent damage in the worst case dissipation situations, i.e. when there is an absence of cooling fluid and/or the electrode is surrounded by tissue.

In the absence of such control, the temperature of the electrode follows an asymptotic curve as shown in FIG. 1. The saline absorbs power until the point of vaporisation is reached at time '$t_1$'. When the saline is vaporised, the active tip temperature rises more rapidly until, at time '$t_2$', active electrode destruction occurs at a temperature of 1600° C. (melting point of platinum). This destruction temperature is indicated by temperature '$T_D$' in FIG. 1. The time taken to reach this temperature after vaporisation occurs is dependent on both thermal capacity and thermal dissipation mechanisms. A low mass electrode heats up faster. The principal dissipation mechanism is infra-red emission and is, therefore, dependent on surface area.

Limitation of peak voltage is used, as described above, to control the applied r.f. power so as to prevent the electrode temperature reaching $T_D$ under all normal operating conditions. It will be appreciated that this limits the rate at which tissue can be removed.

It is an object of the present invention to provide a means of increasing the rate of tissue removal.

SUMMARY OF THE INVENTION

According to a first aspect of the present invention, an electrosurgical generator comprises a source of radio frequency (r.f.) energy, an active output terminal, a return output terminal, a d.c. isolation capacitance between the source and the active output terminal, and a pulsing circuit for the source, wherein the source and the pulsing circuit are arranged to generate a pulsed r.f. output signal at the output terminals, which signal has a peak-to-peak voltage of at least 1250V, a pulse mark-to-space ratio 1:1 or less, and a pulse length of 100 µs or less. The pulse repetition rate is preferably between 5 Hz and 15 kHz or, more preferably, below 2 kHz. Advantageously, the mark-to-space ratio of the modulation is dynamically variable in response to a temperature signal from a temperature sensing arrangement, the signal being representative of the temperature of an electrode when coupled to the active output terminal.

The preferred generator includes a pulse modulator arranged to modulate the r.f. energy so as to produce a pulsed signal having alternate 'off' and 'on' periods during which the peak-to-peak output voltage of the generator is substantially zero and at least 1250V respectively, the duration of the 'on' periods being controlled in response to the temperature signal reaching a predetermined threshold value. When the load impedance drops to 50 ohms the peak current is at least 3 A.

It is possible to control the mark-to-space ratio on a pulse-by-pulse basis by using a temperature sensing arrangement having a response time which is less than the modulation period. Such an arrangement is one which is responsive to thermionic emission from the electrode, detected by monitoring the d.c. offset voltage on the output terminal coupled to the treatment electrode resulting from the thermionic effect.

According to a second aspect of the invention, an electrosurgical generator comprises a source of r.f. energy, a pair of output terminals coupled to the source, and a pulsing circuit for the source, wherein the pulsing circuit and the source are arranged, in a pulsed mode of operation, to deliver to the output terminals a peak current of at least 3 A into a 50 ohm load and a peak-to-peak voltage of at least 1250V into a 1 kilohm load.

According to a third aspect of the invention, an electrosurgery system comprises a generator having a source of radio frequency (r.f.) energy and, coupled to the generator, an bipolar electrosurgical instrument having an electrode assembly with at least a pair of electrodes for operating in a wet field, wherein the generator is adapted to deliver r.f. energy to the electrode assembly as a pulse modulated r.f. signal which, in use with the pair of electrodes immersed in liquid, has a peak current of at least 3 A and a peak-to-peak voltage of at least 1250V.

According to a fourth aspect of the invention, there is provided an electrosurgery system comprising a generator including a source of radio frequency (r.f.) energy and, coupled to the generator, an electrosurgical instrument having a treatment electrode, wherein the system includes an electrode temperature sensing arrangement and the generator is adapted to supply the r.f. energy to the electrode as a pulse modulated r.f. signal, the mark-to-space ratio of the modulation being dynamically variable in response to a temperature signal from the temperature sensing arrangement representative of the electrode temperature.

The generator and system disclosed in this specification make of the property that the tissue removal rate increases disproportionally with the applied peak voltage. Accordingly, by pulsing the output signal and increasing the peak voltage beyond that which would normally create destructive conditions for the electrode, it is possible to increase the tissue removal rate without a corresponding increase in the applied power. The way in which the tissue removal rate varies is best understood by considering some examples. For instance, an electrode using a peak-to-peak voltage of 1250V yields approximately twice the tissue removal rate of an electrode operating at 1000V. Thus if an electrode is driven at a voltage of 1250V peak-to-peak with a 50% duty cycle, the removal rate is approximately equivalent to that achieved with continuous application of a voltage of 1000V peak-to-peak. However, it is possible to use higher voltages still. An electrode normally limited to 1000V peak-to-peak can be operated at up to 1500V peak-to-peak and the removal rate can be doubled again. Thus, an electrode powered at a 50% duty cycle at a voltage of 1500V peak-to-peak will have approximately twice the removal rate of an electrode operating continuously with 1000V peak-to-peak.

Higher-than-normal peak voltages cause higher temperatures when used in a continuous mode of operation. However, in the presence of liquid, the "off" period of a pulsed signal, allows quenching and cooling of the electrode by the liquid, which causes the electrode temperature to remain below the electrode destructive value $T_D$ shown in FIG. 1, despite the higher applied voltage. It follows that if, during treatment, the electrode is used in such a way as to prevent cooling by the quenching effect of the liquid, it is likely to be destroyed as a result of heat accumulation. Such a condition can arise when the electrode is buried in tissue. It is for this reason that it is beneficial to use electrode temperature sensing to limit the application of r.f. energy to the electrode when operating at high peak-to-peak voltages. Conveniently then, the mark-to-space ratio (the duty cycle) of the pulse-modulated r.f. signal is reduced when the temperature signal reaches a predetermined level corresponding to an electrode temperature approaching the temperature at which destruction occurs (usually the melting point of the electrode material). The temperature signal may be derived from the d.c. offset voltage produced at the relevant generator terminal due to thermionic emission at the treatment electrode.

In this way, it is possible to perform electrosurgical removal of tissue at a higher rate than previously, not only due to being able to operate at higher temperature in other than worst case dissipation conditions, but also due to the high removal rate associated with high instantaneous voltage.

It is possible, within the scope of the invention, to drive a treatment electrode at much lower pulse mark-to-space ratios, depending on the applied voltage, the average power delivered, the electrode configuration and the rate at which heat is dissipated from the electrode due to, for instance the rate of flow of fluid adjacent the electrode. Accordingly, advantageous tissue removal rates can be achieved with a duty cycle as low as 5% and peak-to-peak voltages in the region of 3 kV or 4 kV. Indeed, it is possible to achieve rapid tissue removal with instantaneous power levels of up to 10 kW peak currents 20 A (i.e. both within 'on' bursts) and a pulse repetition rate of 2 kHz or higher. The pulse length, i.e. the duration of the 'on' bursts may be as short as 5 ms or even 1 ms. Such pulse lengths may be shorter than the thermal response time constant of the treatment electrode. Particular benefits can be achieved with high instantaneous power and short pulses when high liquid pumping rates are used since with high voltages vaporisation and tissue removal tends to occur very quickly, so that less of the incident energy is lost due to the flow of heated liquid away from the electrode.

Typically, the control circuitry of the generator and the detector are operable to limit the d.c. offset to a predetermined d.c. voltage level in the region of from 50V to 100V. In practice, the actual voltage level depends on electrode configuration and electrode material. Thus, if a platinum electrode is used, the voltage limit is set to that which occurs when the electrode voltage approaches 1600° C., the melting point of platinum.

In a preferred embodiment of the invention, the generator has an output terminal connectible to the treatment electrode and isolated from the r.f. source at d.c., and the detector has (i) a detection input which is connected to the output terminal and (ii) an isolation device connecting the detector to the control circuit. The detector may be powered from the generator r.f. output energy by having a power supply circuit coupled to the generator output terminal and including a rectifier for rectifying the r.f. electrosurgery signal applied to the output terminal. This is permissible since the thermionic effect does not occur until the r.f. output voltage reaches a level consistent with arcing. The fact that the detector does not function at lower voltages is, as a result, no disadvantage. Typically, to achieve isolation at the output of the detector, it comprises an oscillator for generating an alternating measurement signal representative of the d.c. offset, and the isolation device comprises an opto-isolator coupled to receive the alternating measurement signal and to feed it to the control circuit. The preferred detector also includes a reverse polarity d.c. offset detector as a fault condition indicator which can be used to disable the r.f. source when, for instance, in use of a bipolar electrode assembly in a conductive fluid field, a lack of fluid causes d.c. polarity reversal.

According to a further aspect of the invention, there is provided a method of operating an electrosurgery system including an electrosurgical r.f. generator and an electrode assembly having a treatment electrode coupled to the generator, wherein the method comprises applying to the electrode a pulse-modulated r.f. signal produced by the generator, generating a temperature signal indicative of the temperature of the electrode, and dynamically varying at least the mark-to-space ration of the pulse modulation of the r.f. signal in order to control the temperature of the electrode.

According to yet a further aspect of the invention, a method of performing electrosurgical tissue cutting or ablation comprises applying r.f. energy to an electrosurgical instrument so as to promote arcing at a treatment electrode of the instrument, wherein the energy is applied as a pulsed r.f. signal with a peak-to-peak voltage of at least 1250V and a pulse mark-to-space ratio of 1:1 or less. The r.f. energy may be regulated by regulating the mark-to-space ratio dynamically to maximise the temperature of the electrode without substantial electrode damage, the d.c. voltage being limited to a threshold value of less than 100V.

The invention will be described below by way of example with reference to the drawings.

BRIEF DESCRIPTION OF THE DRAWINGS in the drawings.

DETAILED DESCRIPTION OF THE PREFERRED EMBODIMENT

Figure 2:
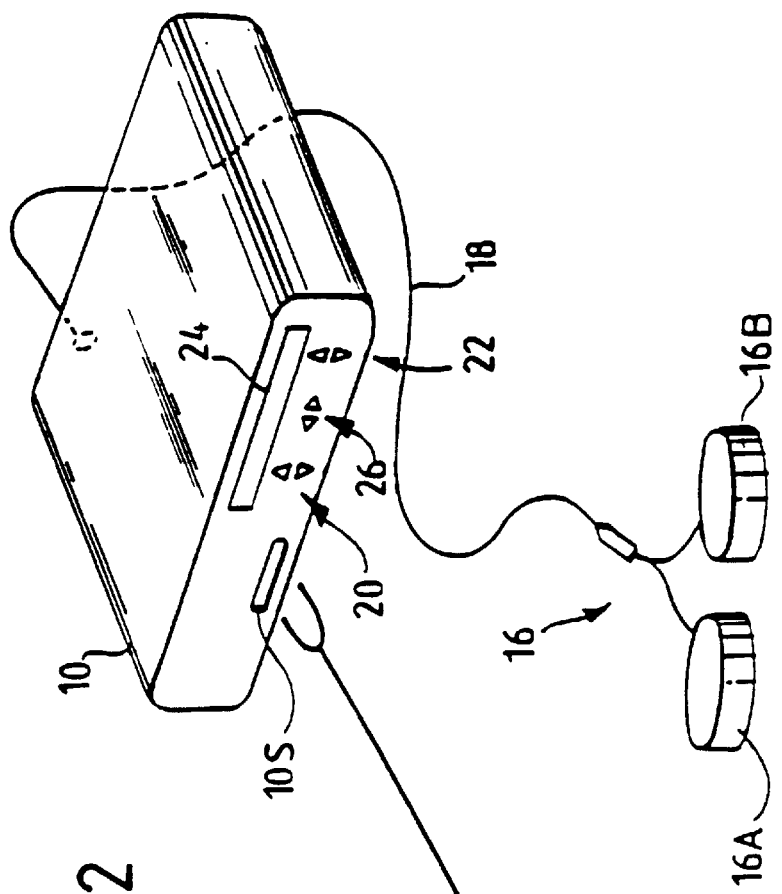
FIG. 2 is a diagram showing an electrosurgery system in accordance with the invention.

The present invention is applicable primarily but not exclusively to wet field electrosurgery. Referring to FIG. 2, the system comprises a generator 10 having an output socket 10S which provides a radio frequency (r.f.) output for an electrosurgical instrument in the form of a handpiece 12 via a connection cord 14. Activation of the generator may be performed from the handpiece 12 via a control connection in cord 14 or by means of a foot switch unit 16, as shown, connected separately to the rear of the generator 10 by a foot switch connection cord 18. In the illustrated embodiment, the foot switch unit 16 has two foot switches 16A and 16B for selecting different generator modes such as a desiccation mode and a vaporisation mode. The generator front panel has push buttons 20 and 22 for setting power levels, which are indicated in a display 24. Push buttons 26 are provided as an alternative means for mode selection.

Figure 3:
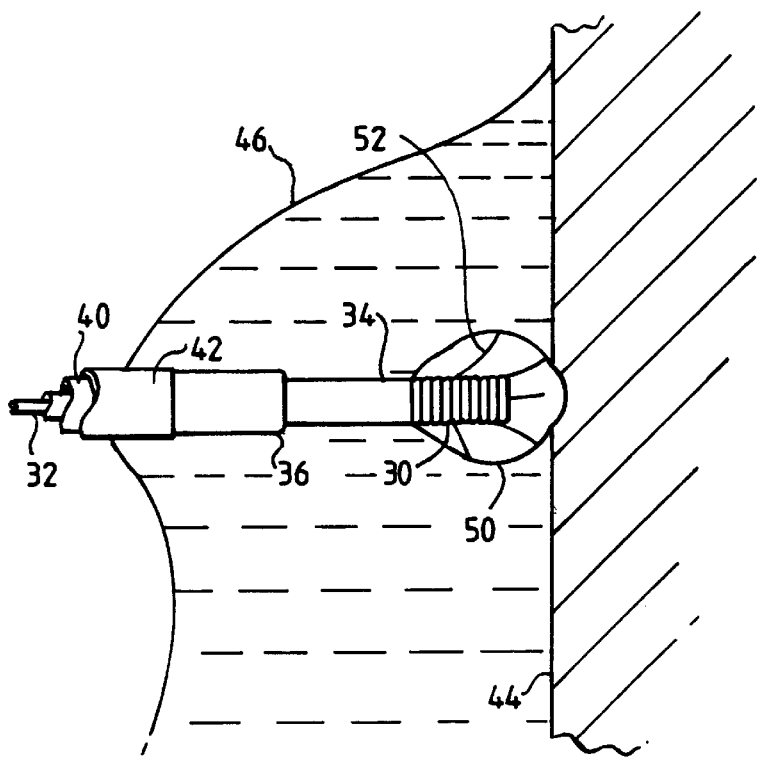
FIG. 3 is a fragmentary view of an electrode assembly for tissue ablation, shown in use immersed in a conductive liquid.

Handpiece 12 mounts a detachable electrode assembly 28 having a dual electrode structure, as shown in the fragmentary view of FIG. 3.

FIG. 3 is an enlarged view of the distal end of the electrode assembly 28. At its extreme distal end the assembly has an active electrode 30 which, in this embodiment, is formed as a coiled wire connected to a central conductor 32. The coil wire may be made of platinum. Proximally of the active electrode 30 and spaced from the latter by a longitudinally and radially extending ceramic insulator 34 is a return electrode 36. The return electrode 36 is arranged coaxially around the inner conductor 32 as a sleeve which extends as a tubular shaft 40 to the proximal end of the assembly 28 (see FIG. 1) where it is connected in the handpiece 12 to a conductor in the connection cord 14. Similarly, the inner conductor 32 extends to the handpiece 12 and is connected to another conductor in cord 14. Insulation between the inner conductor 32 and the return electrode 36 is provided by the insulator 34 which is constructed as a sleeve extending inside the return electrode to insulate an inner extension (not shown) of the active electrode 30 from the return electrode 36. To promote greater power density at the active electrode than at the return electrode, the surface area of the return electrode is considerably greater than that of the active electrode. With regard to typical dimensions, at the distal end of the electrode assembly, the diameter of the return electrode is typically in the region of from 1 mm to 3 mm, with the longitudinal extent of the exposed part of the return electrode being typically between 1 mm and 5 mm and the longitudinal spacing from the active electrode being between 1 mm and 5 mm. The electrode assembly 28 has an insulating sheath 42 which covers shaft 40 and terminates proximally of the ceramic insulator 34 to leave the distal end of shaft 40 exposed as the return electrode 36.

In operation as an instrument for cutting or removing tissue in a conductive fluid field, the electrode assembly 28 is applied as shown in FIG. 3 to the tissue 44 to be treated, the operation site being immersed in a normal saline (0.9% w/v) solution 46 immersing both the active electrode 30 and the return electrode 36.

The electrode assembly is effectively bipolar, with only one of the electrodes (active electrode 30) axially extending to the distal end of the unit. This means that the return electrode, in normal circumstances in a wet field, remains spaced from the tissue being treated and a current path exists between the tissue and the return electrode via the conductive liquid in contact with the return electrode. The conductive liquid 46 may be regarded, as far as the delivery of bipolar electrosurgical energy is concerned, as a low impedance extension of the tissue.

When sufficient r.f. voltage is applied between the electrodes 30, 36, power dissipation in the conductive liquid 46 causes the liquid to vaporize, initially forming small vapour bubbles on the surface of the active electrode 30, which ultimately coalesce until the electrode is completely enveloped in a pocket of vapour 50. Vapour pocket 50 is sustained by discharges 52 across the vapour pocket between the active electrode 30 and the vapour-to-saline interface. The majority of power dissipation now occurs within this pocket with consequent heating of the active electrode, the amount of energy dissipated being a function of the delivered power. By holding the active electrode 30 adjacent the surface of the tissue 44, as shown in FIG. 3, so that the vapour pocket intercepts the tissue surface, tissue removal occurs by cell rupture due to the arcing occurring between the electrode and the tissue.

This mode of operation can be maintained over a comparatively wide range of power levels, but increasing the delivered power beyond this range causes a rapid rise in electrode temperature as described above with reference to FIG. 1, potentially damaging the electrode. The point at which this occurs depends on the speed with which heat can be removed from the electrode which, as will be appreciated, is affected by convection due to flow of the fluid 46 past the electrode 20, the proximity of the electrode 30 to the tissue and, in the worst case, burying of the electrode 30 in the tissue. It follows that, while a peak voltage limit may be established to prevent a runaway temperature rise at the electrode, such limit, to be effective, has to be set at a level which will prevent such a rise in the worst case thermal dissipation conditions.

Figure 1:
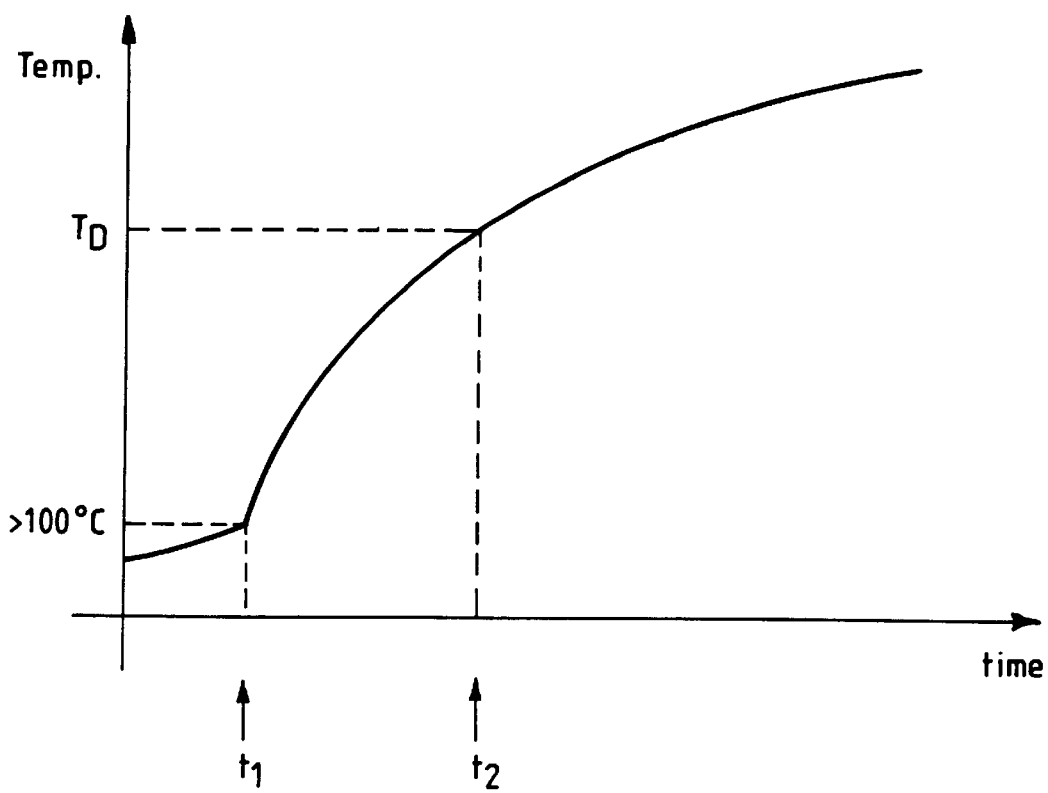
FIG. 1 is a graph showing the thermal response of an electrosurgical electrode to which radio frequency power is applied in an unregulated manner, the electrode being immersed in a conductive liquid.

In describing above the system with reference to FIGS. 1 to 3, the thermal characteristics of the electrode referred to are those obtained with substantially continuous application of r.f. power. The applicants have found that by applying pulse modulation so that an r.f. voltage is applied between the electrode as a pulsed signal in which the pulse is alternately at a predetermined non-zero level and substantially zero, higher levels of tissue ablation can be achieved without the electrode reaching the electrode destruction temperature $T_D$ (see FIG. 1). High power pulsing of the electrode with a peak voltage higher than that obtained when peak voltage is used to limit electrode temperature. This takes advantage of the fact that the tissue removal rate is disproportionate to voltage. For instance, operating the generator at a peak-to-peak voltage of 1250V yields approximately twice the tissue removal rate compared with operation at 1000V. If the generator is operated at 1250V peak-to-peak with a 50% duty cycle, the removal rate is approximately equivalent to that achieved of continuous application of a voltage of 1000V peak-to-peak. However, it is possible to use higher voltages still. A system with an electrode assembly normally limited to 1000V peak-to-peak can be operated up to 1500V peak-to-peak and the removal rate can be doubled again. Thus, an electrode used on a 50% duty cycle with 1500V peak-to-peak will have approximately twice the removal rate of an electrode operating with continuous r.f. power at 1000V peak-to-peak.

Figure 4:
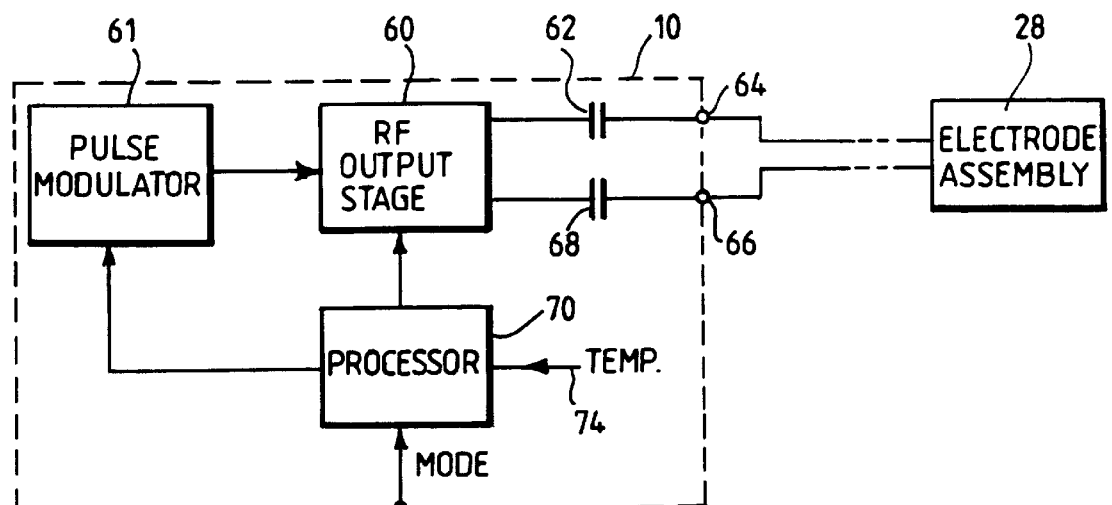
FIG. 4 is an electrical block diagram of the system shown in FIG. 2.

Referring to FIG. 4, in a system in which pulsed r.f. power can be applied from a generator 10 to an electrode assembly 28 as a pulsed signal, an r.f. output stage 60 is coupled to a pulse modulator 61 so that a pulsed electrosurgical signal (typically having a carrier frequency in the range of from 100 kHz to 5 MHz) is fed via a series isolating capacitor 62 to an active output terminal 64 of the generator 10. A return terminal 66 of the generator is also coupled to the r.f. stage, likewise via an isolation capacitor 68.

The pulse modulator 61 is actuated by a processor 70 which, in turn, receives mode signals from the front panel of the generator or the foot switches (see FIG. 1). Accordingly, the generator may have a vaporisation mode in which the r.f. power stage 60 is modulated by the pulse modulator 61 with a mark-to-space ratio of 1:1 or less (i.e. successive "on" times representing a 50% duty cycle or less). The frequency of the modulation is typically 300 Hz. The processor 70 also controls the peak voltage of the r.f. output stage 60 according to mode. In addition, the processor has a temperature signal input 74 allowing control of the pulse modulator 61 in response to electrode temperature, as will be described in detail below.

Figure 5:
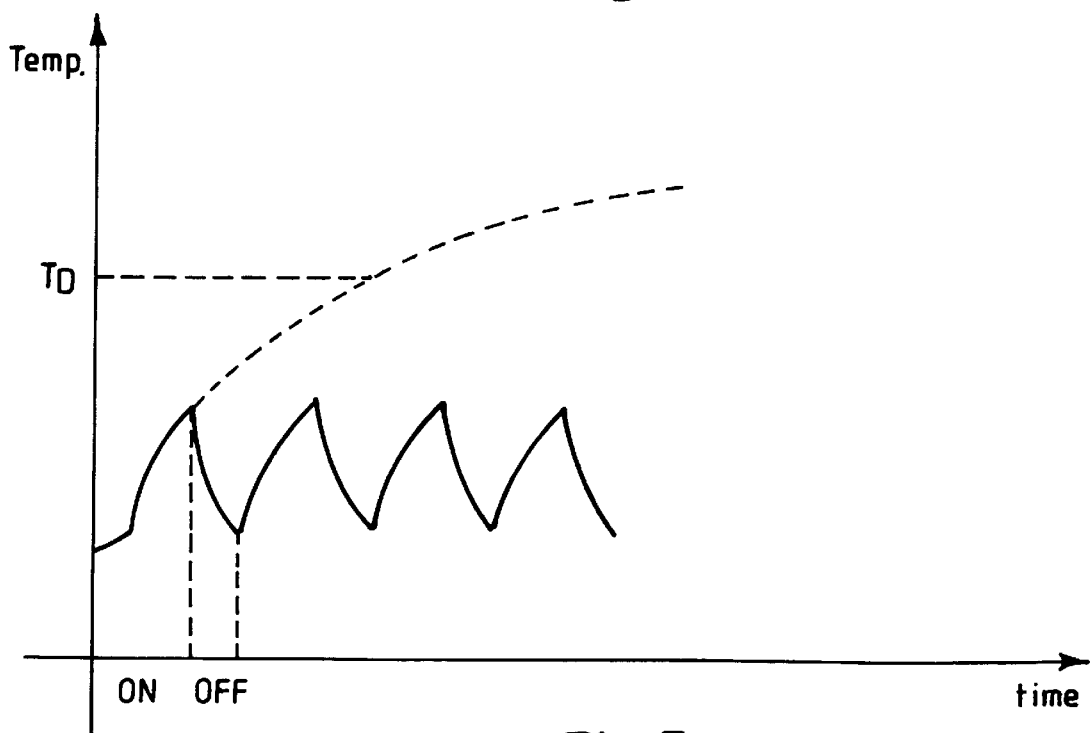
FIG. 5 is a graph showing the variation of electrode temperature with time using the same scales as FIG. 1, but with the applied radio frequency power pulsed.

A representation of the variation of the electrode temperature with time when r.f. power is applied at a relatively high peak-to-peak voltage with 100% pulse modulation depth is shown in FIG. 5. The mark-to-space ratio is 1:1. In other words, power is only applied for 50% of the time. This yields two potential benefits. Compared with continuous 1000V peak-to-peak operation, application of pulsed power at 1000V peak-to-peak results in a reduction in the average delivered power by as much as 25%. Since the peak delivered power is higher (i.e. during the r.f. burst when the pulse modulation is at logic level 1, the electrode is less susceptible to quenching effects caused by high flow rates of saline passed the electrode. This is explained by considering the saline at the surface of the active electrode. The ability to vaporise this saline is defined by the power it absorbs before leaving the electrode surface. When convection due to fluid flow is high, the saline refresh rate is high and, therefore, the power absorbed by per unit volume of saline at the electrode surface is smaller. If the waveform crest factor is increased by the use of modulation, as described above, but with similar average power levels, then the power absorbed per unit volume of saline during each power burst is higher.

The above described advantages are achieved because, during the "off" period of the modulation, the electrode is quenched and cooled. It is for this reason that the electrode temperature never reaches the steady state destructive value $t_D$. If the electrode is used in such a manner that cooling by quenching is interrupted, there is a danger that the electrode will be destroyed by heat accumulation. This condition can arise when the electrode is buried in tissue. Accordingly, in accordance with the invention, the pulsing of the electrosurgical power is performed in conjunction with temperature monitoring, as provided for by the temperature signal input 74 to the process 70 in FIG. 4. The temperature signal applied to the input 74 is produced by an electrode temperature sensing arrangement, which may take a number of forms, for instance, a circuit for measuring a d.c. offset voltage across terminals 74 and 66 due to the thermionic effect occurring when the active electrode becomes very hot.

Processor 70 acts in such a way as to modify the mark-to-space ratio of the pulse modulation generated by pulse modulator 61 according to the level of the electrode temperature signal applies on input 54. Specifically, in this embodiment, a characteristic of the electrode temperature signal applied to the input 74 is compared with a threshold value which is a function of the maximum allowed temperature, so that the pulse modulator applied an "on" signal to the r.f. output stage 60 until the temperature signal reaches the predetermined threshold value, whereupon the r.f. output stage is switched off for a predetermined period.

Figure 6A:
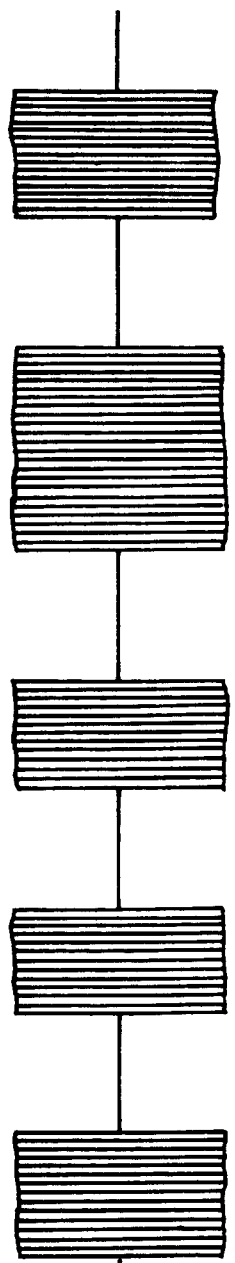
FIGS. 6A and 6B are, respectively, a generator output waveform and an electrode temperature graph showing the effect of varying the mark-to-space ratio according to electrode temperature.
Figure 6B:
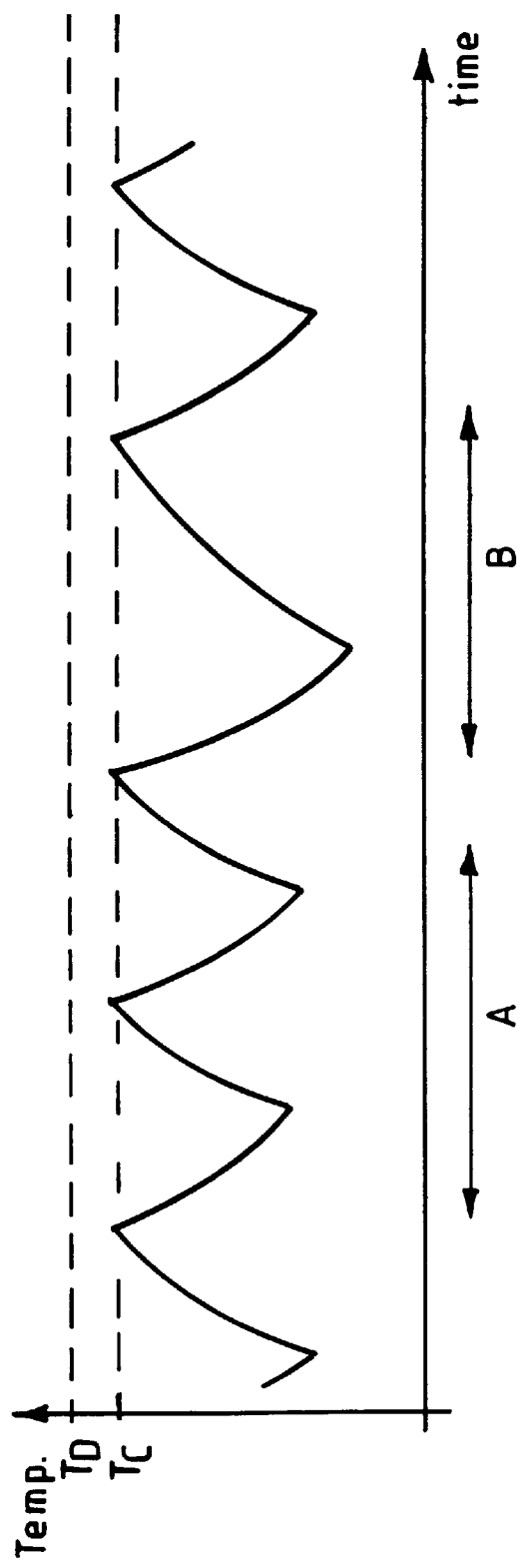

This manner of operating is illustrated in FIGS. 6A and 6B. Since the electrode temperature can be monitored, the "on" burst can be sustained longer than would be possible without such monitoring so that the electrode reaches a higher temperature without fear of electrode burning. The length of each "on" burst is controlled according to the rate at which the electrode is cooled during the "off" periods, e.g. by allowing the burst to continue until a control temperature $T_C$ being a predetermined threshold temperature below the destruction temperature $T_D$. It will be understood that during the period "A" shown in FIG. 6B, the conditions at the electrode reduce the rate of heat dissipation from the electrode, whilst in the period "B" dissipation is increased. Consequently, during period A, the "on" bursts are shorter whereas in period B, they are longer. As explained above, this combination of pulsed operation with temperature feedback allows the use of higher peak voltages without the electrode temperature reaching the destructive level, with a consequent improvement is tissue removal rate. In effect, the modulation is adaptive according to electrode temperature.

The modulation rate is primarily dependent upon the time taken for the vapour pocket around the active electrode to collapse, so that the electrode can be cooled. Ideally, power is reapplied as soon as the quenching occurs, in order that the resulting saline is not lost by either convection or flow. The burst length is preferably sufficiently long that re-establishing the vapour pocket occurs at least within the first half of the "on" burst. Modulation rates of 5 Hz to 2 kHz are appropriate.

As mentioned above, temperature sensing is done indirectly by monitoring the thermionic effect, as will now be described with reference to FIGS. 7A and 7B.

Figure 7A:
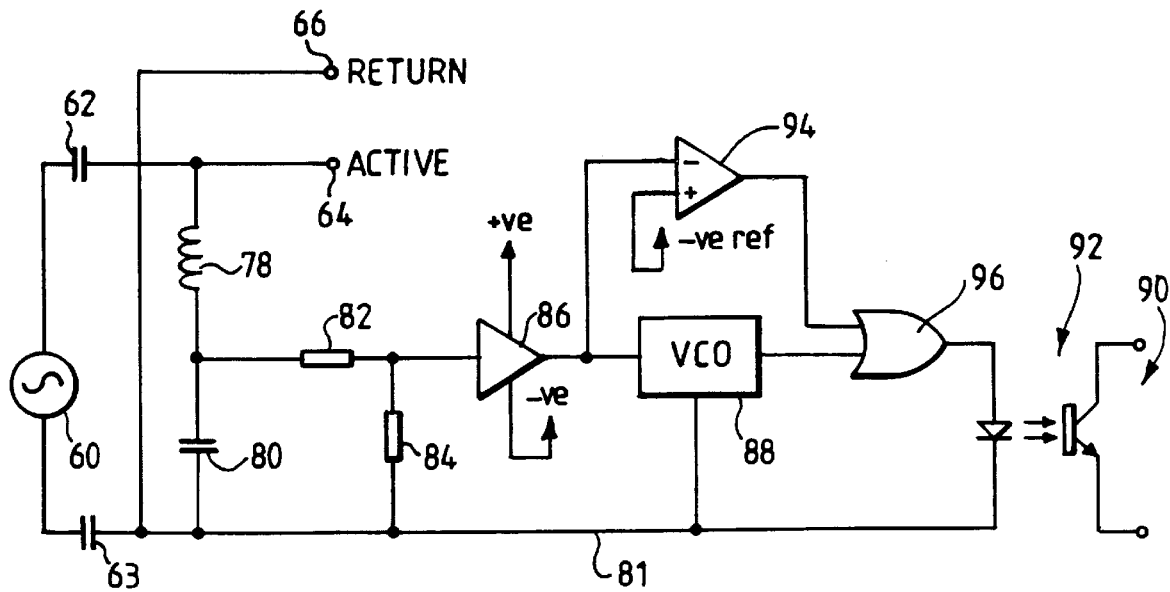
FIGS. 7A and 7B are circuit diagrams of a d.c. offset detector.
Figure 7B:
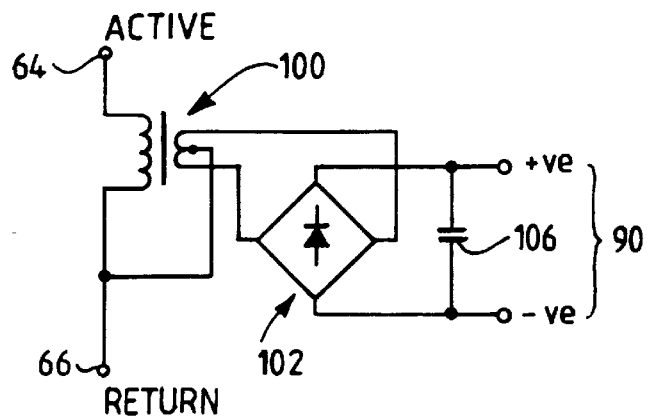

Referring to FIG. 7A, the preferred system in accordance with the invention includes an r.f. output stage in the form of a source 60 delivering an electrosurgical voltage via coupling capacitors 62, 63 between first and second output terminals 64, 66 to which the active and return electrodes of the electrode assembly 28 are respectively connected. When arcing occurs at the active electrode 30, as shown in FIG. 3, thermionic emission from the electrode occurs when the electrode is spaced from the tissue 44, dependent on the temperature of the electrode, leading to the build up of a positive potential on the active output terminal 64. In effect, the combination of the heated active electrode 30, the tissue, the conductive fluid 46, and the return electrode 36 together act as a rectifier, the conductive solution behaving as the anode and the active electrode as the cathode of the rectifier respectively. The hotter the active electrode, the greater is the rectification and the greater the d.c. offset voltage on the output terminal 64 of the generator.

The temperature-dependent positive potential (the d.c. offset voltage) is monitored using a detector connected as a shunt input across the generator output, on the output terminal side of the isolation capacitance. The detector has an input circuit with a series r.f. choke 78 coupled to the output terminal 64, and a smoothing capacitor 80 coupled to the common rail 81 which is connected to the return terminal 66. Therefore, d.c. component of the voltage at the active output terminal 64 accumulates at the junction of the choke 78 and the smoothing capacitor 80 where it is applied to a potential divider 82, 84 which present an input resistance of at least 2 MΩ, and typically between 50 and 100 MΩ. the output of the potential divider 82, 84 is applied to a high impedance buffer 86 the output of which provides a driving signal to a voltage controlled oscillator (VCO) 88. Providing an input impedance in the region of 50 to 100 MΩ yields a detection current in the region of 1 μA for d.c. offsets in the region of 50 to 100V. Maintaining a low detection current has the advantage that nerve stimulation due to a direct current between the target tissue and the return electrode is avoided.

Conversion of the d.c. offset voltage to an alternating signal in the VCO 88 allows the signal to be transmitted to an isolated control circuit (not shown in FIG. 7A) connected to the output 90 of the detector via an opto-isolator 92, for controlling the r.f. energy applied to the generator output terminals so as, for example to limit the offset voltage. An indication of the d.c. offset is communicated in this way across the safety isolation barrier between the output terminals of the generator and the power generating and control circuit. In the control circuitry, the alternating signal can be converted back to a d.c. level using a monostable and low pass filter, or may be counted by a gated counter and conveyed digitally. In either case, the control circuit is arranged to reduce the average output power of source 60 when the d.c. offset voltage reaches a predetermined value (typically within the range 50 to 100V), by altering the mark-to-space ratio of the pulse modulation as described above. Accordingly, by selecting a threshold d.c. offset voltage related to the maximum safe operating temperature of the active electrode, the r.f. power delivered to the active electrode can be maximised in different thermal dissipation conditions. The processor 70 of the generator (see FIG. 4) receives a temperature signal which may be the direct output of the opto-isolator 82, in which case the threshold value for pulse width control is a frequency value, or a frequency-to-voltage converter (not shown) may be interposed, in which case the threshold value is a preset voltage value.

When the bipolar electrode assembly shown in FIG. 3 is used incorrectly, for example when there is insufficient saline around the assembly, it is possible for arcing to occur at the return electrode 36. In such circumstances, the d.c. offset polarity reverses so that the active terminal 64 becomes negative with respect to the return. The detector illustrated in FIG. 7A includes a reverse polarity detection circuit in the form of a comparator 94 bypassing the VCO 88 and having an output coupled to one input of, for instance, an OR-gate 96 the other input of which receives the alternating output from the VCO 88. The other input of the comparator 94 is coupled to a negative voltage reference. Normally, the output of comparator 94 is low, which means that the alternating signal developed by the VCO passes through OR-gate 94 to the opto-isolator 92. However, when the d.c. offset voltage on output terminal 64 of the generator turns negative by more than an amount depending on the negative reference voltage applied to comparator 94, the output of comparator 94 becomes high and OR-gate 96 blocks the alternating signal from the VCO 88, and the lack of an alternating signal applied to the control circuit from the detector output 90 can be used as a fault indication to shut off the r.f. source 60.

In this embodiment, power for the buffer 86, VCO 88, comparator 94, and OR-gate 96 is derived from the r.f. voltage itself delivered to the output terminals 64 and 66 of the generator, avoiding the need for a further isolation barrier. A suitable power supply for this purpose is illustrated in FIG. 7B. A step-down transformer 100 coupled between the output terminals 64 and 66 of the generator drives a bridge rectifier 102 to deliver a d.c. voltage at power supply output terminals 104 across a smoothing capacitor 106. Connection of the secondary winding of the transformer 100 with a centre tap to the return output terminal 66, and thus the common rail of the detector, allows the buffer 86 to be provided with a dual-polarity supply in order to accommodate positive and negative d.c. offset voltages. The fact that deriving power from the r.f. output in this way results in the detector being inoperative at low voltages is no disadvantage since the thermionic effect relied upon as the control stimulus does not occur until the r.f. output voltage of the generator reaches a level consistent with arcing at the active electrode.

Use of the invention is not restricted to wet field (underwater) electrosurgery. Arcing also occurs with monopolar or bipolar electrosurgery instruments in dry field surgery and power can be controlled using the thermionic effect in the same way as described above.

What is claimed is:

1. An electrosurgical generator comprising a source of radio frequency (r.f.) energy, an active output terminal, a return output terminal, a d.c. isolation capacitance between the source and the active output terminal, and a pulsing circuit for the source, wherein the source and the pulsing circuit are arranged to generate a pulsed r.f. output signal at the output terminals, which signal has a peak-to-peak voltage of at least 1250V, a pulse mark-to-space ratio of no greater than 1:1, and a pulse length of no greater than 100 μs.

2. A generator according to claim 1, wherein the pulse repetition rate is between 5 Hz and 15 kHz.

3. A generator according to claim 1, including a d.c. voltage detector connected between the active and return output terminals, and wherein the pulsing circuit forms part of a control circuit configured to control the r.f. energy delivered from the output terminals in response to a d.c. voltage detected by the detector.

4. A generator according to claim 3, wherein the control circuit and the detector are operable to control the delivered r.f. energy so as to limit the d.c. voltage.

5. An electrosurgical generator comprising a source of r.f. energy, a pair of output terminals coupled to the source, and a pulsing circuit for the source, wherein the pulsing circuit and the source are arranged, in a pulsed mode of operation, to deliver to the output terminals a peak current of at least 3 A into a 50 ohm load and a peak-to-peak voltage of at least 1250V into 1 kilohm load.

6. A generator according to claim 5, wherein the pulse repetition rate in the pulsed mode being less than 12 kHz, and wherein the generator is capable of delivering a peak power of at least 200 W in the pulsed mode.

7. An electrosurgery system comprising a generator having a source of radio frequency (r.f.) energy and, coupled to the generator, an bipolar electrosurgical instrument having an electrode assembly with at least a pair of electrodes for operating in a wet field, wherein the generator is adapted to deliver r.f. energy to the electrode assembly as a pulse modulated r.f. signal which, in use with the pair of electrodes immersed in liquid has a peak current of at least 3 A and a peak-to-peak voltage of at least 1250V.

8. A system according to claim 7, wherein the ratio of peak power to average power is greater than 4:1.

9. A system according to claim 8, wherein the ratio of peak power of average power is greater than 20:1.

10. A system according to claim 7, wherein the generator is capable of delivering a peak power of 200 W in a pulsed made of operation, the ratio of peak power is average power being at least 4:1.

11. An electrosurgery system comprising a generator including a source of radio frequency (r.f.) energy and, coupled to the generator, an electrosurgical instrument having a treatment electrode, wherein the system includes an electrode temperature sensing arrangement and the generator is adapted to supply the r.f. energy to the electrode as a pulse modulated r.f. signal, the mark-to-space ratio of the modulation being dynamically variable in response to a temperature signal from the temperature sensing arrangement representative of the electrode temperature.

12. A system according to claim 11, wherein r.f. energy is delivered to the electrode as a pulsed signal having a pulse repetition rate between 5 Hz and 2 kHz and with a peak-to-peak voltage value of at least 1250V.

13. A system according to claim 12, wherein the generator includes a pulse modulator arranged to modulate the r.f. energy so as to produce a pulsed signal having alternate 'off' and 'on' periods during which the peak-to-peak output voltage of the generator us substantially zero and at least 1250V respectively, the duration of the 'on' periods being controlled in response to the temperature signal reaching a predetermined threshold value.

14. A system according to claim 11, wherein the temperature sensing arrangement has a response time which is less than the modulation period.

15. A system according to claim 11, wherein the temperature sensing arrangement is responsive to thermionic emission from the electrode.

16. A system according to claim 15, wherein the temperate sensing arrangement includes a d.c. voltage detector arranged to detect a d.c. offset on the treatment electrode.

17. A system according to claim 16, wherein the temperature sensing arrangement and the pulse modulator are adapted to control the modulation of the generator output signal so as to limit the d.c. offset to a predetermined d.c. voltage level.

18. A system according to claim 17, wherein the predetermined d.c. voltage level is in the region of from 50V to 100V.

19. A system according to claim 11, wherein the mark-to-space ratio is 1:1 or less during at least the majority of the time the generator is activated.

20. A system according to claim 19, wherein the peak-to-peak output voltage is greater than or equal to 1500V.

21. A method of operating an electrosurgery system including an electrosurgical r.f. generator and an electrode assembly having a treatment electrode coupled to the generator, wherein the method comprises applying to the electrode a pulse modulated r.f. signal produced by the generator, generating a temperature signal indicative of the temperature of the electrode, and dynamically varying at least the mark-to-space ratio of the pulse modulation of the r.f. signal in order to control the temperature of the electrode.

22. A method according to claim 21, wherein the pulse repetition rate of the r.f. signal is between 5Hz and 2 kHz with a peak-to-peak voltage of at least 1250V.

23. A method according to claim 22, wherein the pulsed signal has alternate 'on' and 'off' periods during which the peak-to-peak output voltage of the generator is substantially zero and at last 1250V respectively, the duration of the 'on' periods being controlled in response to the temperature signal reaching a predetermined threshold value.

24. A method according to claim 21, wherein the temperature signal is responsive to changes in electrode temperature occurring within one pulse cycle.

25. A method according to claim 21, including detecting a d.c. offset voltage on the treatment electrode due to thermionic emission from the electrode and generating the temperature signal as a function of the offset voltage.

26. A method according to claim 21, wherein the mark-to-space ratio of the pulse modulation is 1:1 or less during at least the majority of the time the r.f. signal is applied to the electrode.

27. A method of performing electrosurgical tissue cutting or ablation in which r.f. energy is applied to an electrosurgical instrument so as to promote arcing at a treatment electrode of the instrument, wherein the energy is applied as a pulsed r.f. signal having a peak-to-peak voltage of at least 1250V, a pulse mark-to-space ratio of no greater than 1:1 and a pulse length of no greater than 100 μs.

28. A method according to claim 27, wherein the mark-to-space ratio is dynamically regulated to maximise the temperature of the electrode without substantial electrode burning.

29. A method according to claim 27, wherein the electrosurgical instrument has an electrode assembly with at least two electrodes, including an active electrode and a return electrode, wherein the tissue cutting or ablation is performed in the presence of a conducting liquid supplied to the site of the operation such that electrosurgical currents pass from the active electrode to the return electrode through said liquid, and wherein application of the pulsed r.f. signal causes a layer of vapour to form and collapse repeatedly at the active electrode, the layer being formed when the pulsed signal is 'on' and collapsing when the said signal is 'off'.

30. A method according to claim 27, wherein the peak current is at least 3 A.

* * * * *